United States Patent [19]

Koyama

[11] Patent Number: 4,984,260

[45] Date of Patent: Jan. 8, 1991

[54] RADIATION DIAGNOSTIC DEVICE

[75] Inventor: Katsuhide Koyama, Otawara, Japan

[73] Assignee: Kabushiki Kaisha Toshiba, Kawasaki, Japan

[21] Appl. No.: 281,337

[22] Filed: Dec. 8, 1988

[30] Foreign Application Priority Data

Dec. 11, 1987 [JP] Japan ................................ 62-311872

[51] Int. Cl.$^5$ ............................................. G03B 42/02
[52] U.S. Cl. ................................... 378/173; 378/172; 378/181
[58] Field of Search .................................. 250/327.2; 378/172–174, 181

[56] References Cited

U.S. PATENT DOCUMENTS

| | | | |
|---|---|---|---|
| 4,597,097 | 6/1986 | Suzuki | 378/174 |
| 4,659,929 | 4/1987 | Fujiwara et al. | 378/173 |
| 4,667,102 | 5/1987 | Koyama et al. | 378/181 |
| 4,785,179 | 11/1988 | Iwasaki | 250/327.2 J |
| 4,793,812 | 12/1988 | Sussman et al. | 358/473 |
| 4,836,527 | 6/1989 | Wong | 271/251 |
| 4,847,497 | 7/1989 | Mori | 250/327.2 C |

FOREIGN PATENT DOCUMENTS 2802971 7/1978 Fed. Rep. of Germany ...... 378/172

*Primary Examiner*—Janice A. Howell
*Assistant Examiner*—David P. Porta
*Attorney, Agent, or Firm*—Oblon, Spivak, McClelland, Maier & Neustadt

[57] ABSTRACT

A radiation diagnostic device wherein different kinds of picture image record media can be used and the performance is improved. The radiation diagnostic device which includes a photographing station in which radiograph information of an object for inspection is irradiated upon a picture image record medium to make radiation photographing of the object for inspection comprises a first storing station for storing therein first and second different picture image record media, a first transporting system for alternatively taking out one of first and second picture image record media from the first storing station and transporting the same to the photographing station, a second storing station for storing therein first and second picture image record media after photographing, and a second transporting system for transporting a first or second picture image record medium after photographing from the photographing station to the second storing station. With the radiation diagnostic device, the transporting systems are commonly used for first and second picture image record media.

8 Claims, 4 Drawing Sheets

RADIATION DIAGNOSTIC DEVICE

BACKGROUND OF THE INVENTION

1. Field of the Invention

This invention relates to a radiation diagnostic device wherein radiograph information of an object for inspection is irradiated upon a picture image record medium to make radiation photographing.

2. Description of the Prior Art

Exemplary ones of conventional radiation diagnostic devices are devices of the type wherein an X-ray is irradiated upon an object for inspection to make X-ray photographing of the object for inspection.

One of the type just mentioned is a device of the type wherein X-ray photographing is carried out while an X-ray fluoroscopic image is being observed in accordance with an X-ray photographing method of the film intensifying screen type wherein a large number of X-ray films loaded in position in the device are taken out one by one and a pair of intensifying screens are disposed on and closely contacted with front and reverse faces of a thus taken out X-ray film. The device of the type just mentioned is particularly called cassetteless X-ray snapshot photographing device.

In contrast to such a cassetteless X-ray snapshot photographing device, there is another device which can photograph using a fluorescent sheet called an imaging plate and carrying a fluorescent substance of an accelerated phosphorescence thereon. An imaging plate on which picture image information is recorded by the device just mentioned is sent to a picture image reading device where the recorded picture image is read out. In the picture image reading device, a face of the imaging plate is scanned by a beam of excitation light to cause accelerated phosphorescent light to be emitted from the imaging plate, and the accelerated phosphorescent light is converted into electric signals which are then processed to obtain a picture image which is superior in diagnostic aptitude.

To the contrary, a device has not yet been provided wherein an X-ray film and an imaging plate can both be used for X-ray photographing. Further, while an imaging plate can be used repeatedly, the life of such an imaging plate is comparatively short because no special attention is paid to prevention of damaging to a surface of the imaging plate in a transporting system for an imaging plate.

SUMMARY OF THE INVENTION

It is an object of the present invention to provide a radiation diagnostic device wherein different types of picture image record media can be used and the performance is improved.

In order to attain the object, according to the present invention, a radiation diagnostic device which includes a photographing station in which radiograph information of an object for inspection is irradiated upon a picture image record medium to make radiation photographing of the object for inspection comprises a first storing station for storing therein first and second different picture image record media, a first transporting system for alternatively taking out one of first and second picture image record media from the first storing station and transporting the same to the photographing station, a second storing station for storing therein first and second picture image record media after photographing, and a second transporting system for transporting a first or second picture image record medium after photographing from the photographing station to the second storing station.

With the radiation diagnostic device, the transporting systems are used commonly for first and second picture image record media. Accordingly, the performance of the radiation diagnostic device is improved.

The above and other objects, features and advantages of the present invention will become apparent from the following description and the appended claims, taken in conjunction with the accompanying drawings.

DESCRIPTION OF THE PREFERRED EMBODIMENT

Figure 1:
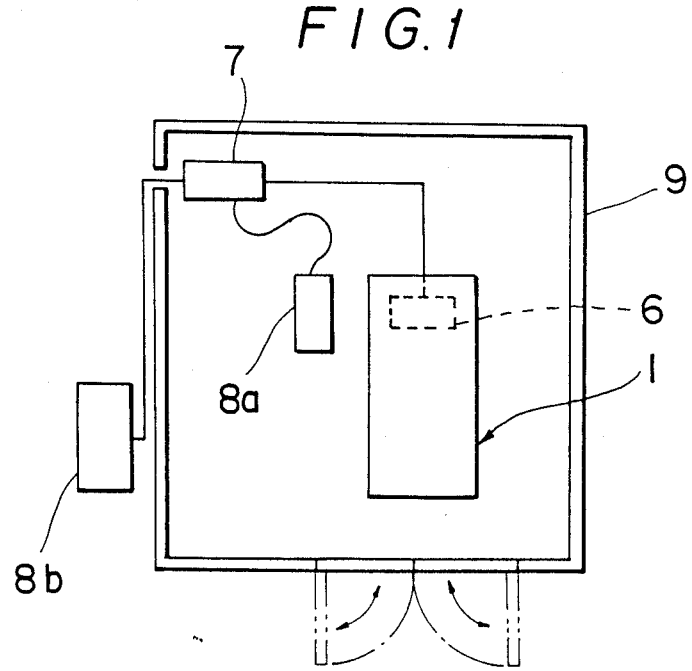
FIG. 1 is a block diagram of a radiation diagnostic system in which a radiation diagnostic device according to the present invention is incorporated.

Referring first to FIG. 1, there is shown a radiation diagnostic system in which a radiation diagnostic device according to the present invention can be incorporated. The radiation diagnostic system shown includes a radiation diagnostic device such as, for example, an X-ray diagnostic device 1, a controlling means 6 for controlling signals to be transmitted between an external device and the X-ray diagnostic device 1, an X-ray barrier 9 containing lead therein, a contactless operation panel 8a located inside the X-ray barrier 9, a main operation panel 8b located outside the X-ray barrier 9, and a control box 7 for changing over transmission of signals from the contactless operation panel 8a and the main operation panel 8b to control the X-ray diagnostic device 1.

Figure 2:
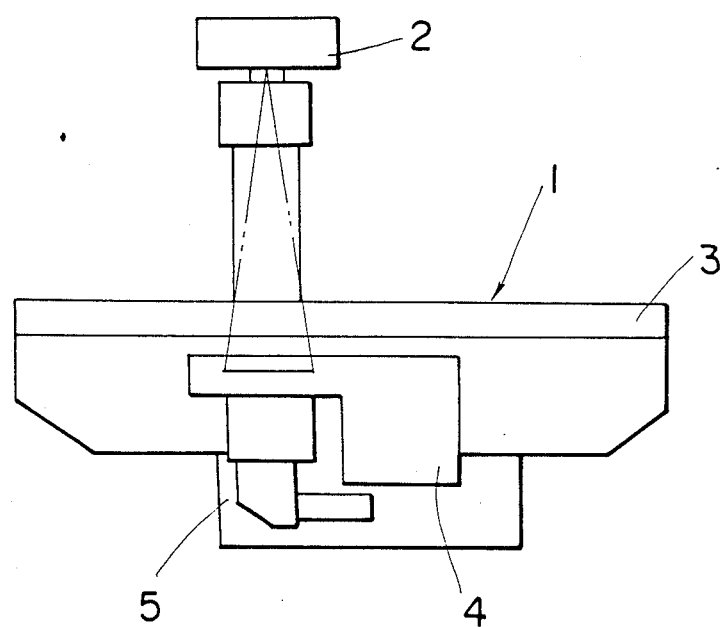
FIG. 2 is a schematic plan view of a radiation diagnostic device showing a preferred embodiment of the present invention.

Referring now to FIG. 2, the X-ray diagnostic device 1 to which the present invention is applied includes an X-ray tube 2 for irradiating an X-ray to an object for inspection (patient), a top plate 3 disposed below the X-ray tube 2 for receiving an object for inspection thereon, an X-ray snapshot photographing device 4 disposed below the top plate 3 and including a transporting route for a picture image record medium, and an imaging system 5 including an image intensifier for converting a component of an X-ray irradiated from the X-ray tube 2 and transmitted through an object for inspection into a visible ray and a television camera system for photographing an image of a visible ray.

It is to be noted that two kinds of X-rays for an X-ray fluoroscopic image and for photographing can be emitted from the X-ray tube 2.

Figure 3:
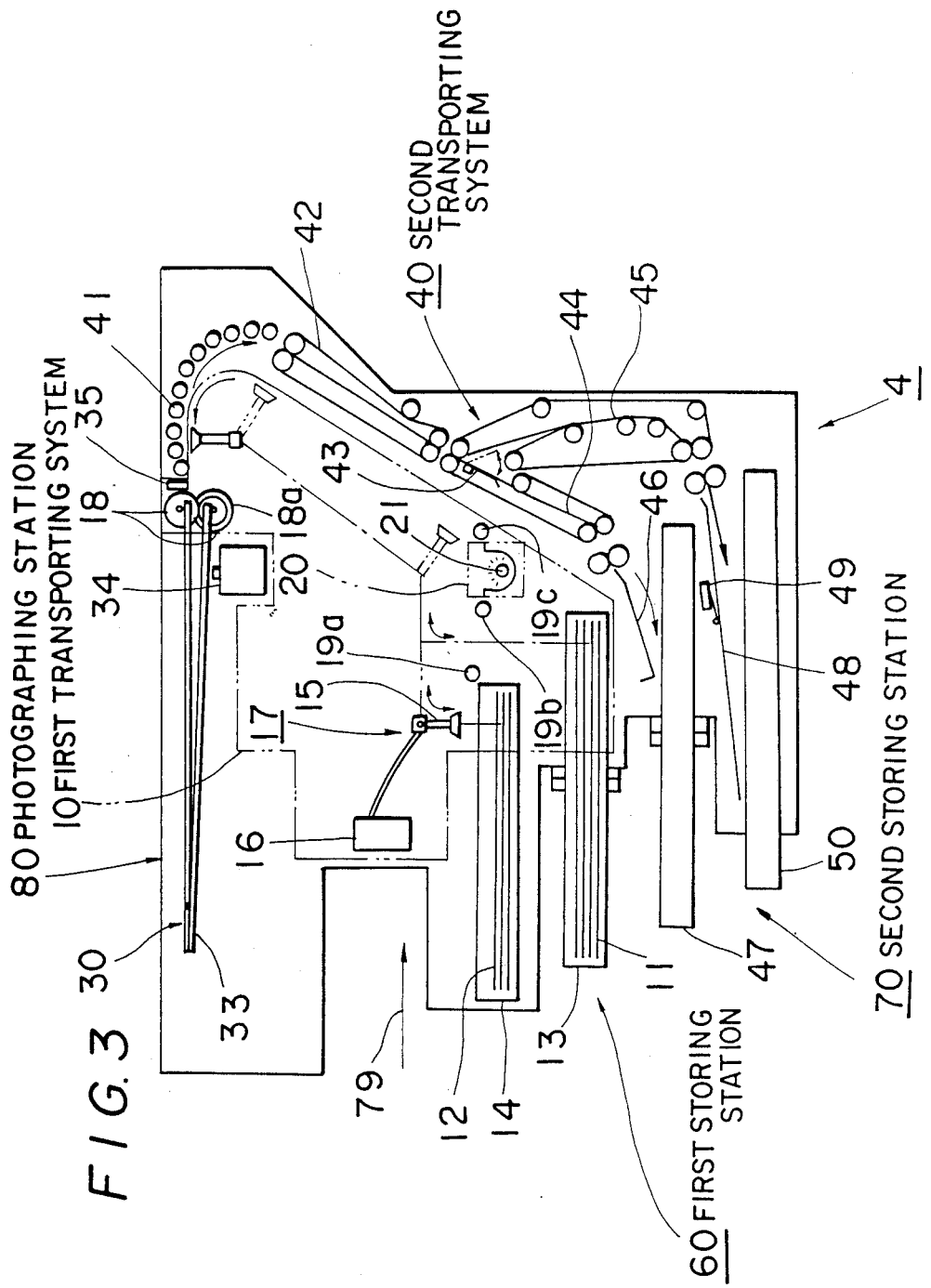
FIG. 3 is an enlarged side elevational view of part of the radiation diagnostic device of FIG. 2.

Referring now to FIG. 3, the X-ray snapshot photographing device 4 generally includes a first transporting system 10, a secondary erasing station 20, a closely contacting station 30, a second transporting system 40, a first storing station 60 and a second storing station 70.

The first storing station 60 is provided for storing therein picture image record media before photographing while the second storing station 70 is provided for storing therein picture image record media after photographing. Such picture image record media here include first and second picture image record media of different types. The first picture image record media may be X-ray films while the second picture image record media may be imaging plates. The first storing station 60 includes a film feed magazine 13 serving as a first storage means for storing X-ray films 11 therein, and an imaging plate storing tray 14 serving as a second storage means for storing imaging plates 12 therein. Meanwhile, the second storing station 70 includes a film take-up magazine 47 serving as a first storage means for storing X-ray films after photographing therein, and an imaging plate take-up magazine 50 serving as a second storage means for storing imaging plates therein. All of the storage means 13, 14, 47 and 50 of the first and second storing stations 60 and 70 are removably mounted on a body of the radiation diagnostic device from the same direction, for example, from the left side in FIG. 3 so as to facilitate supply and removal of picture image record media.

Meanwhile, the first transporting system 10 is designed to alternatively take out X-ray films 11 and imaging plates 12 one by one from the first storing station 60 and transport them to a photographing station 80. The first transporting system 10 includes a taking out mechanical section 17 including a pair of vacuum attracting tubes 15 and a vacuum pump 16, a pair of forwarding members 18 for receiving therebetween a picture image record medium taken out by the taking out mechanical section 17 and forwarding it to the closely contacting station 30, a stepping motor 18a for driving the forwarding members 18, a stepping motor controlling means not shown, and an optical sensor 35 of the reflecting type for detecting an optical sensor 35 of the reflecting type for detecting an amount of a picture image record medium being fed to the closely contacting station 30 in order to control the feed amount.

When a picture image record medium is forwarded toward the closely contacting station 30, a leading end of the picture image record medium is detected by the optical sensor 35 of the reflecting type. In response to a detection signal from the optical sensor 35, the stepping motor controlling means not shown controls the stepping motor 18a to drive the forwarding members 18 to rotate so that the picture image record medium is forwarded further until a trailing end thereof is detected by the optical sensor 35. In response to a detection signal from the optical sensor 35, the stepping motor controlling means not shown delivers a predetermined number of pulses to the stepping motor 18a so that the picture image record medium may be fed to and stopped at a predetermined position. It is to be noted that which one of an X-ray film 11 and an imaging plate 12 should be taken out by the taking out mechanical section 17 may be determined by one of a pair of switches provided on the operation panel 8a of 8b.

The secondary erasing station 20 is disposed near a central location of the first transporting system 10. The secondary erasing station 20 is provided for erasing noise components of an imaging plate and includes a lamp 21 for irradiating light upon an imaging plate taken out from the imaging plate storing tray 14 by the taking out mechanical section 17 only when the imaging plate passes over the secondary erasing station 20.

Three pairs of rollers 19a, 19b and 19c made of a soft, spongy material such as, for example, a polyurethane material are disposed adjacent an imaging plate taking out port of the imaging plate storing tray 14 and adjacent the opposite ends of the secondary erasing station 20. The rollers 19a, 19b and 19c are provided for supporting movement of an imaging plate while preventing damaging to a surface of the imaging plate.

Figure 4:
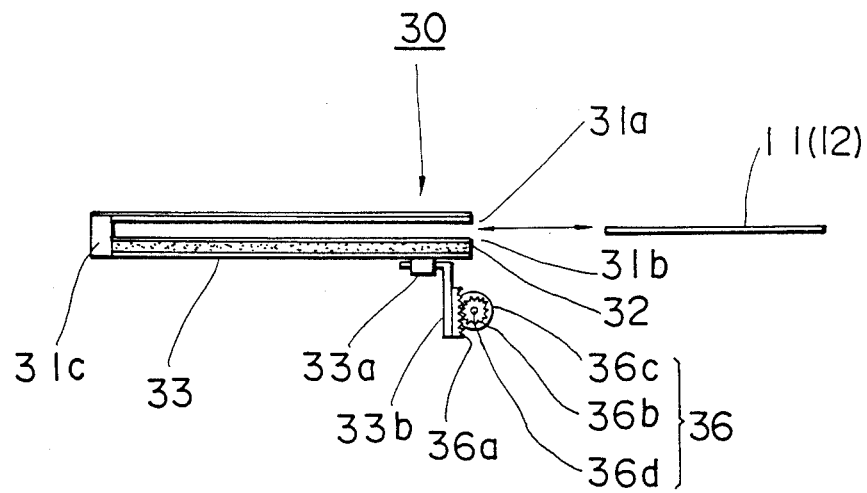
FIG. 4 is a schematic view showing detailed structure of a closely contacting station of the radiation diagnostic device of FIG. 2.
Figure 5:
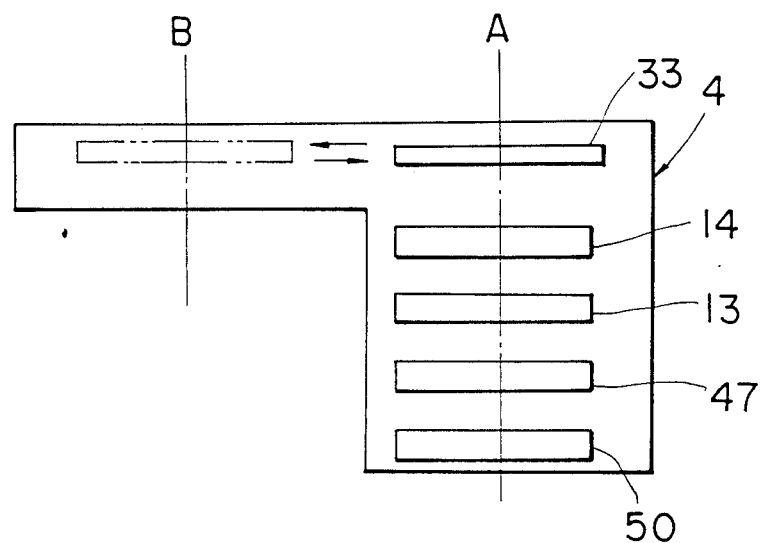
FIG. 5 is a schematic front elevational view of an X-ray snapshot photographing device of the radiation diagnostic device of FIG. 2 as viewed in the direction indicated by an arrow mark 79 in FIG. 3.

Meanwhile, the closely contacting station 30 belongs to the photographing station 80 and is designed to receive a picture image record medium introduced thereto by the forwarding members 18, feed it to a predetermined photographing position directly below the X-ray tube and hold it in a closely contacting relationship thereon to permit X-ray fluoroscopic image information of an object for inspection to be recorded (X-ray photographed) on the picture image record medium. FIG. 4 shows detailed structure of the closely contacting station 30. Referring to FIG. 4, the closely contacting station 30 includes a closely contacting plate 33 composed of a front face intensifying screen 31a and a reverse face intensifying screen 31b and a flexible polyurethane sponge plate 32 for making the closely contacting or retaining force uniform, and an opening and closing actuating mechanism 36 for opening or closing the closely contacting plate 33 around a location denoted at 31c in FIG. 4. The opening and closing actuating mechanism 36 includes a rack 36a mounted on a lever 33b secured to the closely contacting plate 33 by means of a fixing member 33a, a pinion 36b held in meshing engagement with the rack 36a, and a motor 36c having an output power shaft 36d on which the pinion 36b is securely mounted. Thus, a driving force of the motor 36c is transmitted to the rack 36a by way of the pinion 36b to open or close the closely contacting plate 33. After the closely contacting plate 33 is opened by the opening and closing actuating mechanism 36, a picture image record medium (an X-ray film 11 or an imaging plate 12) will be placed between the intensifying screens 31a and 31b. The closely contacting plate 33 is mounted for movement in a direction perpendicular to the plane of FIG. 4. FIG. 5 is a schematic view of the X-ray snapshot photographing device 4 as viewed in the direction indicated by an arrow mark 79 in FIG. 3. The closely contacting plate 33 is moved, after it has received a picture image record medium therein, from an initial position A to a photographing position B, and then after X-ray photographing is carried out at the photographing position B, the closely contacting plate 33 is moved back to its initial position A.

It is to be noted that a name printer 34 is disposed at the photographing station 80 as shown in FIG. 3 so that patient information including a name, the date of birth and so on of an object for inspection (patient) and some other photographing information may be printed on an X-ray film. Printing of various information by the name printer 34 is performed immediately after the closely contacting plate 33 in which an X-ray film is held has been returned to its initial position A.

Figure 6:
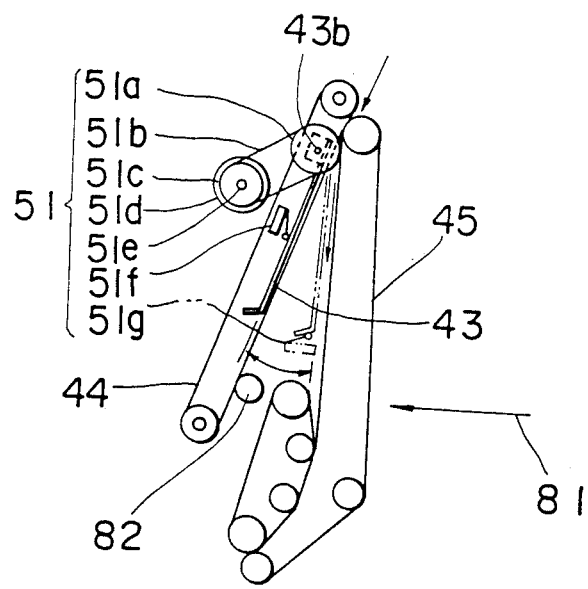
FIG. 6 is an enlarged side elevational view showing details of a transporting route change-over means of the radiation diagnostic device of FIG. 2.
Figure 7:
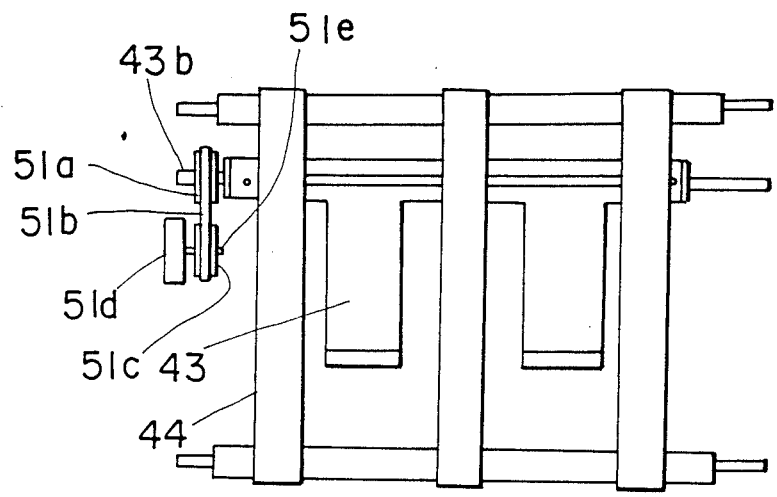
FIG. 7 is a schematic view showing the transporting route change-over means as viewed in the direction indicated by an arrow mark 81 in FIG. 6.

The second transporting system 40 is provided for transporting a first or second picture image record medium after photographing from the photographing station 80 to the second storing station 70, and includes a plurality of rollers 41, a first pair of transporting belts 42, a second pair of transporting belts 44 and a third pair of transporting belts 45. The rollers 41 are made of a soft, spongy material such as, for example, a polyurethane material and are provided for introducing a picture image record medium after photographing taken out by the closely contacting plate 33 to the first transporting belts 42 while preventing damaging to the picture image record medium. The rollers 41 are individually supported for rotation on a frame not shown or the like. A transporting route change-over means 43 is provided for the second transporting belts 44. By changing over of a route by the transporting route change-over means 43, a picture image record medium after photographing forwarded from the first transporting belts 1 is alternatively held between the second transporting belts 22 or the third transporting belts 45. FIG. 6 shows the transporting route change-over means 43 in an enlarged scale while FIG. 7 shows the transporting route change-over means 43 as viewed in the direction indicated by an arrow mark 81 in FIG. 6. Referring to FIGS. 6 and 7, the transporting route change-over means 43 is mounted for pivotal motion in opposite directions indicated by a double-sided arrow mark 82 around a shaft 43b. The transporting route change-over means 43 is connected to be driven to pivot by a pivotally driving means 51 shown in FIGS. 6 and 7. The pivotally driving means 51 includes a toothed pulley 51a securely mounted on the shaft 43b, a motor 51d serving as a driving source for pivotal motion of the transporting route change-over means 43, another toothed pulley 51c securely mounted on an output power shaft 51e of the motor 51d, a toothed belt 51b extending between and around the toothed pulleys 51a and 51c, and a pair of push type switches 51f and 51g located at the opposite ends of the transporting route change-over means 43 in the directions indicated by the arrow mark 82 for detecting a position of the transporting route change-over means 43.

When an "X-ray film" is selected by one of the selection switches on the main operation panel 8b or the contactless operation panel 8a shown in FIG. 1, the transporting route change-over means 43 is positioned at a position in which it presses the witch 51f as shown by solid lines in FIG. 6 so that a picture image record medium (in this instance, an X-ray film) is fed by the second transporting belts 44. To the contrary, when an "imaging plate" is selected by the other of the selection switches, power is transmitted from the motor 51d via the pulley 51a and 51c and the belt 51b to the transporting route change-over means 43 so that the transporting route change-over means 43 is moved to a position at which it presses the other switch 81g as shown in two-dot chain lines in FIG. 6. Consequently, a picture image record medium 8 (in this instance, an imaging plate) will be fed by the third transporting belts 45.

Referring again to FIG. 3, a film hammering plate 46 is located above the film take-up magazine 47 so that an X-ray film transported thereto by the second transporting belts 44 may be accommodated completely into the film take-up magazine 47 by a film guiding action and a film hammering action of the film hammering plate 46. Meanwhile, an imaging plate forcing plate 48 is located above the imaging plate take-up magazine 50 so that an imaging plate transported thereto by the third transporting belt 45 may be accommodated completely into the imaging plate take-up magazine 50 by a forcing in action of the imaging plate forcing plate 48. A bar code reader 49 for reading a bar code applied to a rear face of an imaging plate is disposed at an upper portion of the imaging plate forcing plate 48, and information of a bar code read by the bar code reader 49 is delivered to a picture image reading device not shown which is provided for reading picture image information recorded on an imaging plate. Such bar code information may include information regarding a patient, information regarding photographing conditions, and so on.

Subsequently, operation of the radiation diagnostic device having such a construction as described above will be described.

Where an "imaging plate" is selected by way of one of the selection switches on the operation panel 8a or 8b, an imaging plate 12 is taken out from within the imaging plate storing tray 14 by the attracting tubes 15 and then transported to the position of the forwarding members 18 by way of the secondary erasing station 20. Then, the imaging plate 12 is forwarded to a position between the intensifying screens 31a and 31b of the closely contacting plate 33 by a forwarding action of the forwarding members 18 (refer to FIG. 4). Subsequently, the closely contacting plate 33 is moved from the initial position A to the photographing position B while holding the imaging plate 12 therein (refer to FIG. 5). At the photographing position B, X-ray radiograph information of an object for inspection (patient) is recorded on the imaging plate 12 (X-ray photographing). It is to be noted that the attracting tubes 15 have been returned to their initial positions till then and are already in a condition prepared for subsequent taking out of a next imaging plate. After completion of the X-ray photographing, the closely contacting plate 33 is returned to its initial position A while the imaging plate after photographing is forwarded toward the second transporting system 40 by a forwarding action of the forwarding members 18 (i.e., by rotation in the opposite direction to that of the preceding rotation). The imaging plate after photographing is then held between and transported by the first transporting belts 42 under the guidance of the rollers 41. Since an "imaging plate" is selected by the one selection switch on the operation panel 8a or 8b as described hereinabove, the transporting route change-over means 43 is positioned as shown by two-dot chain lines in FIG. 6. As a result, the imaging plate after photographing forwarded from the first transporting belts 42 is then fed by the third transporting belts 45 and soon accommodated into the imaging plate take-up magazine 50 by a forcing in action of the imaging plate forcing plate 48. Thereupon, a bar code on the imaging plate after photographing is read out by the bar code reader 49. Information of the bar code thus read is transferred to the picture image reading device.

It is to be noted that when X-ray photographing with an imaging plate is to be performed repetitively several times, the sequence of operations described above will be repeated.

Subsequently, operation of the radiation diagnostic device when an "X-ray film" is selected by the other selection switch on the operation panel 8a or 8b will be described.

Where an "X-ray film" is selected by the other selection switch, an X-ray film 11 is taken out from within the film feed magazine 13 and transported to the position of the forwarding members 18 by the attracting tubes 15. The X-ray film 11 is then forwarded to a position between the intensifying screens 31a and 31b of the closely contacting plate 33 by a forwarding action of the forwardly members 18 in a similar manner as in the case of the imaging plate described hereinabove (refer to FIG. 4). The X-ray film 11 thus forwarded is fed from the initial position A to the photographing position B while being held in the closely contacting plate 33, and at the photographing position B, X-ray transmission information of an object for inspection is recorded on the X-ray film 11 (X-ray photographing). After completion of the X-ray photographing, the closely contacting plate 33 is returned to the initial position A, and immediately after then, patient information of the object for photographing (patient), photographing information and so on are printed on the X-ray film after photographing by the name printer 34. After then, the X-ray film after photographing is forwarded toward the second transporting system 40 by a forwarding action of the forwarding members 18 and then held between and transported by the first transporting belts 42 by way of the rollers 41. Since an "X-ray film" is selected by the other selection switch on the operation panel 8a or 8b as described above, the transporting route change-over means 43 is positioned as shown by solid lines in FIG. 6. As a result, the X-ray film after photographing forwarded by the first transporting belts 42 is fed to the second transporting belts 44 and soon accommodated into the film take-up magazine 47 by a film guiding action and a hammering action of the film hammering plate 46.

It is to be noted that when X-ray photographing with an X-ray film is to be performed repetitively several times, the sequence of operations described above will be repeated.

Thus, the radiation diagnostic device of the present embodiment described above can be constructed with a reduced size and at a reduced cost because the first and second transporting systems 10 and 40 are commonly used for an X-ray film (first picture image record medium) and an imaging plate (second picture image record medium) in such a manner as described above.

Further, since a soft material such as a polyurethane material is applied to each of contacting portions of the first and second transporting systems 10 and 40 at which they are to contact with an X-ray film or an imaging plate, damaging to an X-ray film or an imaging plate can be prevented, and particularly where an imaging plate is used, there if an advantage that the imaging place will have a long life.

Besides, since all of the storage means of the first and second storing stations 60 and 70, that is, the film feed magazine 13, imaging plate storing tray 14, film take-up magazine 47 and imaging plate take-up magazine 50 are removably mounted from the same direction on the body of the radiation diagnostic device, there is an advantage that picture image record media (X-ray films and imaging plates) can be readily supplied into and removed from the device body and accordingly the operability is high.

Moreover, with the radiation diagnostic device of the embodiment described hereinabove, since an X-ray film or an imaging plate is alternatively held in a closely contacting relationship in the same closely contacting plate including the X-ray film intensifying screens, whether, for example, an X-ray film or an imaging plate is to be used, there is no necessity of selecting one of specific devices for handling the different picture image record media.

Accordingly, since the radiation diagnostic device of the present embodiment can handle two different kinds of picture image record media as the photographing station and the transporting route are commonly used for the two kinds of picture image record media, the radiation diagnostic device is improved in performance.

Further, since the radiation diagnostic device includes the rollers for preventing damaging to a surface of an imaging plate, the life of the imaging plate is elongated.

While the preferred embodiment of the present invention has been described so far, it will be apparent to one of the ordinary skill in the art that many changes and modifications can be made to the embodiment without departing from the spirit and scope of the invention as set forth herein. For example, while an X-ray film is used as a first picture image record medium and an imaging plate is used as a second picture image record medium, some other picture image record media may be used as such a first or second picture image record medium.

We claim:

1. A radiation diagnostic device which includes a photographing station in which radiograph information of an object for inspection is irradiated upon a picture image record medium to make radiation photographing of the object for inspection, comprising a first storing station for storing therein first and second different picture image record media, a first transporting system for alternatively taking out one of first and second picture image record media from said first storing station and transporting the same to said photographing station, a second storing station for storing therein first and second picture image record media after photographing, and a second transporting system for transporting a first or second picture image record medium after photographing from said photographing station to said second storing station, wherein each of said first and second storing station includes a first storing means for storing first picture image record media therein, and a second storing means for storing second picture image record media therein.

2. A radiation diagnostic device according to claim 1, wherein a spongy member is applied to each of contacting portions of said first and second transporting systems at which said first and second transporting systems are to be contacted with a first or second picture image record medium.

3. A radiation diagnostic device according to claim 1, wherein said first and second storing means of said first and second storing stations are all removably mounted from the same direction on a body of said radiation diagnostic device.

4. A radiation diagnostic device according to any one of claims 1 or 2 or 3, wherein an X-ray film is used as a first picture image record medium while an imaging plate is used as a second picture image record medium.

5. A radiation diagnostic device according to claim 4, wherein said photographing station includes a closely contacting plate including a pair of X-ray film intensifying screens so that an X-ray film or an imaging plate may be alternatively held in a closely contacting relationship between said X-ray film intensifying screens.

6. A radiation diagnostic device according to claim 1 wherein said second transporting system includes pivotally mounted changeover means pivotal for selectively routing a respective record medium to one or another of said first and second storing means of said second storing station.

7. A radiation diagnostic device according to claim 6 wherein said first transporting system comprises suction means movable between said first storing station and said photographing station for attracting and transporting alternate ones of said first and second picture image record media.

8. A radiation diagnostic device according to claim 6 including means for pivoting said change over means as a function of which of said first and second picture image record media is being transported by said second transporting system.

* * * * *